United States Patent [19]

Von Gentzkow et al.

[11] Patent Number: 4,550,204

[45] Date of Patent: Oct. 29, 1985

[54] METHOD AND APPARATUS FOR THE MANUFACTURE OF N,N'-BIS-(AROYL)HYDRAZINES

[75] Inventors: Wolfgang Von Gentzkow, Kleinsendelbach; Manfred Schmiedel, Nurnberg-Grossgründlach; Reinhold Tussing, Redwitz, all of Fed. Rep. of Germany

[73] Assignee: Siemens Aktiengesellschaft, Berlin and Munich, Fed. Rep. of Germany

[21] Appl. No.: 474,175

[22] Filed: Mar. 10, 1983

[30] Foreign Application Priority Data

Mar. 24, 1982 [DE] Fed. Rep. of Germany ....... 3210859

[51] Int. Cl.$^4$ ............................................ C07C 102/06
[52] U.S. Cl. .................................. 564/134; 564/149; 564/150
[58] Field of Search .................... 564/134, 150, 149

[56] References Cited

U.S. PATENT DOCUMENTS

| | | | |
|---|---|---|---|
| 3,110,696 | 11/1963 | Dexter | 564/149 |
| 3,773,830 | 11/1973 | Dexter | 564/150 |
| 3,849,492 | 11/1974 | Brunetti et al. | 564/150 |
| 3,884,874 | 5/1975 | Rosenberger et al. | 564/150 |
| 3,931,103 | 1/1976 | Hardy | 564/150 |
| 3,993,622 | 11/1976 | Brunetti | 564/150 |

FOREIGN PATENT DOCUMENTS

| | | | |
|---|---|---|---|
| 0047423 | 3/1982 | European Pat. Off. | 564/150 |
| 1593902 | 7/1981 | United Kingdom | 564/150 |
| 0282313 | 9/1970 | U.S.S.R. | 564/150 |

OTHER PUBLICATIONS

Kirk–Othmer *Encyclopedia of Chem. Tech.*, 2nd ed., 1969, vol. 18, pp. 564–588.

*Primary Examiner*—Charles F. Warren
*Assistant Examiner*—John A. Sopp
*Attorney, Agent, or Firm*—Kenyon & Kenyon

[57] ABSTRACT

The invention relates to a method and apparatus for the manufacture of N,N'-bis-(aroyl)hydrazines from hydrazine and arylcarboxylic acid alkyl esters in the presence of catalysts. According to the invention, the reaction ingredients are reacted in a substantially stoichiometric mass ratio in an inert medium of low volatility which is liquid to wax-like under reaction conditions, in a suitable reactor equipped with a centrifugal disc and connected to a cycling, separating and draining-off system and a dispersion head to form a paste-like product. The paste-like compound can be used as a metal deactivator in polyolefin which is in direct contact with copper, for instance, in cable and wire insulation.

15 Claims, 1 Drawing Figure

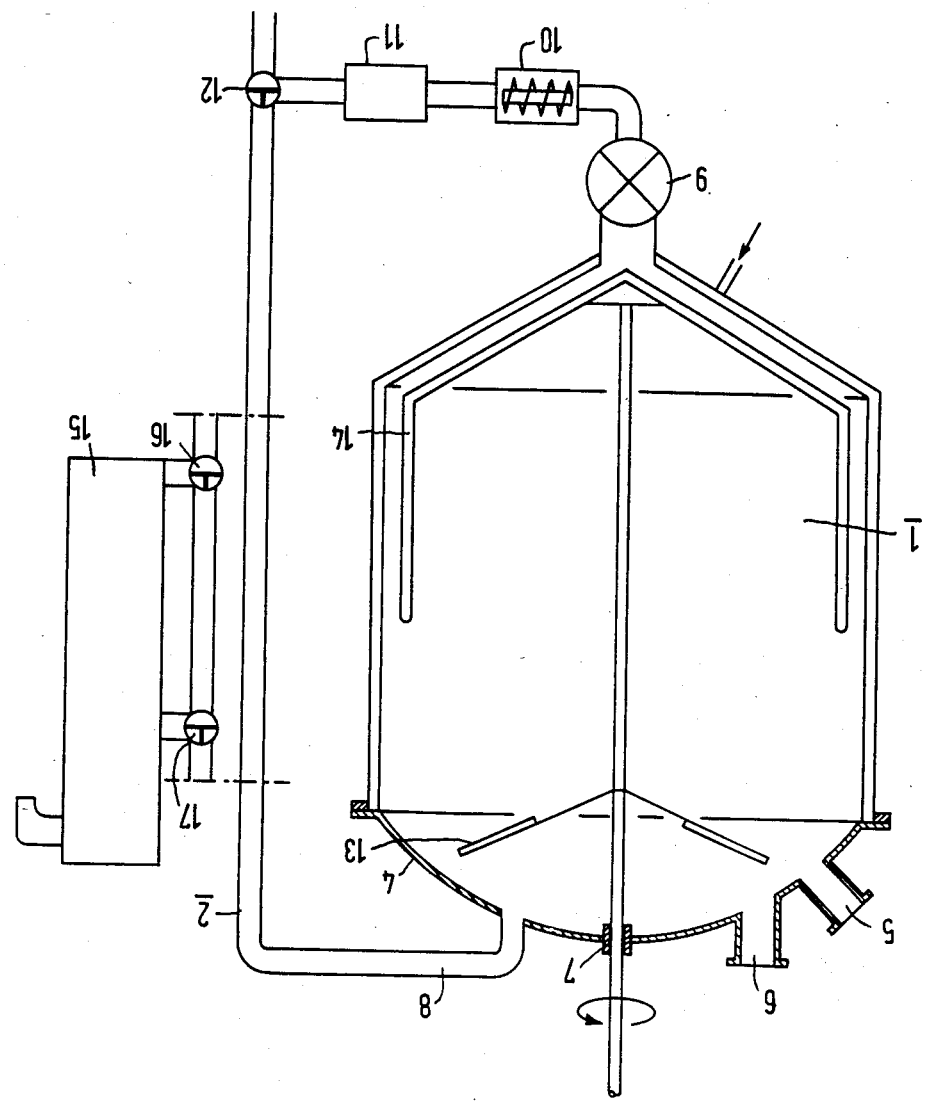

METHOD AND APPARATUS FOR THE MANUFACTURE OF N,N'-BIS-(AROYL)HYDRAZINES

BACKGROUND OF THE INVENTION

The invention relates to a method for the manufacture of N,N'-bis-aroyl hydrazines by catalytic reaction of aryl carboxylic acid alkyl esters with hydrazine or aroyl hydrazine in an inert medium of low voldtility.

It is known to use derivatives of N,N'-bis-salicyloyl hydrazine to prevent thermo-oxidative copper-catalyzed degradation of polyolefins (U.S. Pat. Nos. 3,110,696; 3,843,492 and British Pat. No. 1,593,902).

According to known preparation methods (U.S. Pat. Nos. 3,849,492 and 3,993,622), N,N'-bis-salicyloyl hydrazines can be obtained by reaction of salycylic acid with hydrazide by adding thionyl chloride and pyridine to salicylic acid in chlorobenzene and then adding hydrazide. The products obtained still contain starting components and must be purified by recrystallization. The resulting N,N'-bis-salicyloyl hydrazine is employed as a metal deactivator for polymers. Its production in this manner, however, can cause eye irritation and eye damage because of exposure during preparation and use.

According to the method of U.S. application Ser. No. 173,409, N,N'-bis-salicyloyl hydrazines can also be produced by reaction of salicylic-acid alkyl esters with hydrazine or salicylic-acid hydrazide, optionally in the presence of nucleophilic and/or electrophilic catalysts. For N,N'-bis-salicyloyl hydrazine obtained in this way, eye irritations occur only in reduced form.

It is known from U.S. application Ser. No. 294,032 that the N,N'-bis-salicyloyl hydrazine yield can be increased considerably if hydrazine or salicylic acid hydrazide is reacted in one to ten fold excess relative to salicylic-acid alkyl ester and in the presence of a halide, hydroxide or oxide of boron, aluminum or zinc at temperatures up to 150° C. If boron oxide is used as the catalyst, the product is obtained with especially high purity and, according to tests with rabbit eyes, irritates and damages the eye even less than the products obtained heretofore. The product N,N'-bis-salicyloyl hydrazine is present at the end of the reaction as crystal paste in excess alkyl ester. It is drawn off, washed with alcohol and dried in a vacuum.

With all these methods, N,N'-bis-salicyloyl hydrazine in powder form is eventually produced which can get into human eyes by dust formation during the work-up and technical processing, and can cause eye sickness.

It is, therefore, an object of the invention to prevent contamination of the personnel during the manufacture and technical utilization of N,N'-bis-salicyloyl hydrazines in such applications as metal deactivators for polymers. A further object is to obtain a simplification of the technical manufacturing method.

SUMMARY OF THE INVENTION

These and other objects are achieved by the invention which is directed to a process for preparing a nonirritating bis aroyl hydrazine composition. This process is accomplished by reacting the ingredients namely, hydrazine or an aroyl hydrazine with an aryl carboxylic acid alkyl ester at a nearly stoichiometric mass ratio in an inert medium of low volatility which is liquid to wax-like under reaction conditions to form a paste-like product dispersion, and removing the volatile reaction components from the dispersion by subjecting it to a vacuum. A paste is obtained which contains the bis-(aroyl)hydrazine metal deactivator, is colored by secondary products, and in such form can be mixed with polymers. The aryl groups in the aroyl hydrazine and aryl carboxylic acid ester are preferably phenyl or naphthyl radicals, which are substituted by OH, Cl, Br, alkyl of 1 to 18 carbon atoms, alkenyl with 3 to 18 C-atoms or alkoxy with 1 to 18 carbon atoms. The alkyl group of the ester can be 1 to 5 carbons in length.

The invention is further directed to an apparatus especially designed for the practise of the process of the invention. The apparatus includes a vacuum system, reactor, a dispersing head, a three-way recycle valve at the bottom, a centrifugal disc inside the reactor for producing a thin film on the reactor wall, a recycle pump and a reactor heater.

BRIEF DESCRIPTION OF THE DRAWING

FIG. 1 shows a schematic plan of the reactor apparatus.

DETAILED DESCRIPTION OF THE INVENTION

For some applications, subsequent purification of the paste-like product by extraction has been found advantageous. Suitable extraction media are aliphatic alcohols up to 5 carbons. The extraction is preferably performed with an alkanol of 1 to 2 carbons.

According to the invention, the reaction is carried out in a reactor that can be heated. The starting components are added to the reactor together with the inert medium of low volatility which is liquid to wax-like under reaction conditions. The alcohol produced during the reaction is continuously distilled off by a column distillation which permits the monitoring of the reaction cycle. After the reaction is completed, the reaction mixture paste with crystalline product is cycled through the reaction vessel by pumping it in a vacuum from the bottom of the reactor into the top of the reactor after passing through a dispersion head. As it enters the reactor, the paste is conducted to the reactor wall by a centrifugal shield fastened to the stirrer. The paste runs along the reactor wall as a thin film, is outgassed in the process and is freed of the volatile residues of the reaction such as alcohol. Then, it is distributed directly into shipping casks by switching the three-way valve at the reactor bottom. With this reaction process which takes place with nearly quantitative yield, all steps up to the cask filling operation can be carried out in one device without the danger of contaminating personnel.

Furthermore, the manufacturing method according to the invention can be adapted to appropriate applications in which the final product can be used in unpurified condition or if required it can also be purified in the reactor without exposure to operating personnel.

Suitable media of low volatility, which can be used as reaction medium to wax-like under the reaction conditions, include aliphatic hydrocarbons of low volatility and polyolefins of a low molecular weight range such as 500 to 150,000 mw. These include extender oils, petrolates, paraffins, mineral oils, synthetic oils, waxes and low-molecular polymers, especially polyisobutene.

Suitable catalysts for the reaction process according to the invention are electrophilic and in particular, Lewis acids, for instance, halides, hydroxides and oxides of boron, aluminum and zinc.

A further subject of the invention is the apparatus for implementing the foregoing method, which is characterized by the following parts: a reaction vessel 1 for reacting hydrazine or aroyl hydrazine and aryl carboxylic acid alkyl ester in an inert medium of low volatility which is liquid to wax-like under the reaction conditions, and for purifying the reaction products, a device 2 for pumping, separating and tapping off, a dispersion head 11 for homogenizing the crystal paste, a centrifugal disc 13 inside the reactor for producing a thin film and removing the volatile components and, optionally, an interposed separator 15.

As shown in FIG. 1, details of the apparatus according to the invention includes reactor 1 and a separating, tapping-off and pumping back system, which may comprise separator 15 which is connected to the pumping system by three-way valves 16 and 17. The reactor 1 is provided with a vacuum-tight rotary transmission 7 with stirrer 14 and centrifugal disc 13, a filling stub 5, an opening 6 for the distilling hood and a tapping-off or inlet pipe 8. The reactor can be heated and cooled. Valve 9 is designated as a bottom valve which can be opened for pumping and cycling. A worm pump 10 and a dispersion head 11 complete the cycle circuit. Three-way valve 12 makes it possible to select cycling or distribution of the paste-like reaction product to shipping casks.

Elaborate personnel work protection and filter equipment for the exhaust air are unnecessary for the operation of the apparatus according to the invention since the product never comes into contact with the external environment during processing. The product made in accordance with the invention, which is present as a paste, can be worked directly into polymers which are to be protected against catalytic influences of copper. The products made in accordance with the invention thus are used to particular advantage as metal deactivators in hydrocarbon compounds which contact copper or copper alloys, such as polyolefins for cable and wire insulation, lubricants and cooling oils with a mineral oil base. Working the paste-like mass which contains the metal deactivator, into polyolefins can be accomplished by the customary methods such as directly admixing, optionally also with other additives such as oxidation inhibitors, softeners, fillers and the like. A very fast and homogenous distribution of the metal deactivator in the polyolefin is accomplished thereby in a simple manner.

The process of the invention which is fully set forth by the foregoing description will be illustrated in further detail with the aid of the following examples.

EXAMPLE 1

Preparation of Bis(Salicyloyl)hydrazine in Vaseline 0.5 kg (10 mol) hydrazine hydrate was heated with 3.040 kg (20 mol) salicylic acid methyl ester and 2.714 kg vaseline in a protective gas such as nitrogen or argon in the apparatus according to the invention. The water-methanol mixture produced was continuously distilled-off from the reaction mixture. After about three hours, the reaction temperature had risen to 120° C. and approximately half of the quantity of methanol expected theoretically and the entire amount of water were distilled off (0.5 kg). The hydrazide was present in the vaseline as a crystal product in paste. The heating was continued after 30 g boron trioxide was added and the temperature was kept at 150° C. The remaining methanol (0.320 kg) was distilled off. After about three hours, the reaction was complete as determined by the amount of methanol distilled off.

The reaction apparatus was then evacuated, the bottom valve was opened and the crystal paste was recirculated by the pump and the disperser head. The crystals were comminuted by the head and distributed as a thin film at the upper part of the vessel wall by the centrifugal shield. The residual methanol was outgassed and removed from the thin film. The disperser homogenized the paste.

During the pumping, the temperature was lowered to 80° C. After one hour, when the paste was homogeneous and freed of all volatile components, the paste was pumped directly into the packing cask by changing the position of the three-way valve.

The yield was 80% of the theoretical amount of N,N'-bis-salicyloyl hydrazine.

EXAMPLE 2

Bis(Salicyloyl)Hydrazine in Polyisobutene 50 parts by weight hydrazine hydrate was heated with 304 parts by weight salicylic acid methyl ester in 230 parts by weight polyisobutene (viscosity at 20° C.: 22,000 m Pas) to about 90° C. while stirring vigorously. (Reflux cooler).

After 2 hours, the water and methanol formed were distilled-off by a column, the reaction mixture was treated with 3 parts by weight boron trioxide and heated to a temperature of about 140° to 150° C. while stirring. Methanol produced during the further course of the reaction was continuously distilled-off by a column. After about 3 hours, the reaction was completed. The reaction mixture, which was now viscous, was cooled down to 50° to 60° C. and washed with alcohol until decolorized. The yellow-colored alcohol phase was decanted from the viscous phase.

After separating the washing alcohol, evacuation and drying at about 100° C. were performed. 460 parts by weight of a colorless viscous paste was obtained, consisting of 230 parts by weight N,N'-bis-(salicyloyl)hydrazine (85%) and 230 parts by weight polyisobutene. By dissolving the polyisobutene with methylene chloride and boiling-out the remaining solid matter with methanol, N,N'-bis-(salicyloyl)hydrazine with a melting and decomposition range of 305° to 310° C. was obtained.

EXAMPLE 3

Bis(Salicyoyl)hydrazine Preparation With Paraffin 152 parts by weight salicyclic acid hydrazide was heated with 152 parts by weight salicylic-acid methyl ester and 3 parts by weight boron trioxide in 230 parts by weight paraffin (viscosity at 60° C.: 100 m Pa s) to 140° to 150° C. while stirring vigorously. Methanol produced during the reaction was distilled off by a column. After about 3 hours, the reaction was completed. The now viscous reaction mixture was cooled down to 50° to 60° C., treated with alcohol (methanol or ethanol) and the mixture was stirred very vigorously at about 50° to 60° C. The yellow-colored alcohol phase was decanted from the viscous paste and the process was repeated until discoloration was complete. After separating the washing alcohol, drying in a vacuum at about 100° C. was performed. 460 parts by weight of a colorless viscous paste was obtained, consisting of 230 parts by weight N,N'-bis(salicyloyl)hydrazine (85% yield) and 230 parts by weight paraffin. By dissolving the paraffin with methylene chloride and boiling-out the solid matter with methanol, N,N'-bis(salicyloyl)hydrazine with a melting and decomposition range of 305° to 310° C. was obtained.

EXAMPLE 4

Bis(Aroyl)Hydrazine Preparations With Paraffin 10 mol hydrazine hydrate was heated with 20 mol arylcarboxylic acid alkyl ester and 2.7 kg liquid paraffin in a protective gas in the apparatus according to the invention. The alcohol-water mixture produced was continuously distilled-off from the reaction mixture by a column. After about 1 to 3 hours, the reaction temperature had risen to above 100° C. and half of the theoretically calculated quantity of the alcohol liberated in a complete reaction and the entire amount of water contained in the hydrazine hydrate were distilled off.

After adding 30 g boron oxide, heat was applied to raise the temperature to 150° to 200° C. The residual alcohol produced was distilled off. After about 2 to 3 hours, the reaction was complete, as can be determined from the distilled amount of alcohol.

The apparatus was then evacuated, the bottom valve was opened and the crystal paste was homogenized and freed of volatile components by means of the disperser and the degassing device. During this process, the temperature of the paste was lowered to 50° to 60° C. Thereafter, alcohol was added and the mixture was stirred most vigorously for about 10 minutes at 50° to 60° C. The yellow-colored alcohol phase was separated from the viscous phase and the process was repeated until the paste was decolored.

After the washing alcohol was separated, evacuation and drying at about 100° C. were performed. Nearly theoretical yields of a colorless viscous phase were obtained. By dissolving the paraffin in methylene chloride and washing the remaining solids with methanol, the products listed in the Table of the following formula were obtained with the yields given:

| $R^1$ | $R^2$ | $R^3$ | Yield in % | mp° |
|---|---|---|---|---|
| H | H | H | 92 | 235 |
| Cl | H | OH | 87 | 345 |
| H | OCH$_3$ | OH | 91 | 310 |

What is claimed is:

1. A method for the manufacture of N,N'-bis-(aroyl)-hydrazines by catalytic reaction of an aryl carboxylic acid alkyl ester with hydrazine or aroylhydrazine as reaction ingredients, which comprises: reacting the reaction ingredients at a substantially stoichiometric mass ratio and in an inert medium of low volatility which is liquid to wax-like under the reaction conditions and is a non-solvent for the reaction ingredients and product, to form a paste-like product dispersion and freeing the dispersion of volatile reaction components by applying a vacuum to the dispersion.

2. A method according to claim 1, comprising performing the reaction steps under conditions which isolate the steps from the environment.

3. A method according to claim 1, comprising using hydrazine or salicylic acid hydrazide and salicylic acid alkyl esters as the reaction ingredients.

4. A method according to claim 1 comprising purifying subsequently the paste-like reaction product by extraction with a polar organic solvent.

5. A method according to claim 4 comprising carrying out the extraction with an aliphatic alcohol of 1 to 5 carbons.

6. A method according to claim 1 comprising using polyisobutene as the inert medium.

7. A method according to claim 1 comprising using paraffin as the inert medium.

8. A method according to claim 1 comprising using boron trioxide or boron trihalide as the catalyst.

9. A method according to claim 1 comprising conducting the reaction of the ingredients at a temperature from slightly above ambient to a temperature slightly below the decomposition point of the product.

10. A method according to claim 9 comprising employing a temperature up to 280° C.

11. A method according to claim 1 comprising combining the ingredients in an inert medium, heating the reaction mixture, removing volatile reaction products until the theoretical amounts are reached, and spreading the reaction paste product onto a hot surface under a vacuum to remove residual volatile reaction product.

12. A method according to claim 11 comprising adding the catalyst to the reaction mixture after a portion but not all of the volitale reaction products have been removed.

13. A method according to claim 1 wherein the catalyst is a halide, oxide or hydroxide of boron, aluminum or zinc.

14. A method according to claim 1 wherein the inert medium comprises a hydrocarbon of low volatility and a molecular weight of from about 500 to about 150,000.

15. A method according to claim 14 wherein the hydrocarbon is selected from an extender oil, petrolate, paraffin, mineral oil, synthetic oil, wax, low molecular weight polyolefin and polyisobutylene.

* * * * *